United States Patent
Reed

(10) Patent No.: US 8,123,355 B2
(45) Date of Patent: Feb. 28, 2012

(54) APPARATUS FOR DETERMINING PRESCRIPTION FOR READING LENSES FOR EYES WITH MILD AMD

(76) Inventor: Roger Glenn Reed, Indianapolis, IN (US)

( * ) Notice: Subject to any disclaimer, the term of this patent is extended or adjusted under 35 U.S.C. 154(b) by 0 days.

(21) Appl. No.: 12/854,373

(22) Filed: Aug. 11, 2010

(65) Prior Publication Data

US 2011/0242489 A1    Oct. 6, 2011

Related U.S. Application Data

(60) Provisional application No. 61/319,559, filed on Mar. 31, 2010.

(51) Int. Cl.
*A61B 3/04* (2006.01)
*A61B 3/10* (2006.01)
*A61B 3/02* (2006.01)

(52) U.S. Cl. ......... 351/229; 351/205; 351/222; 351/227

(58) Field of Classification Search .................. 351/229, 351/205–206, 210, 221–226, 200, 227
See application file for complete search history.

(56) References Cited

U.S. PATENT DOCUMENTS 5,104,214 A * 4/1992 Sims ............................ 351/235
5,335,419 A * 8/1994 Marshall ......................... 33/28

* cited by examiner

*Primary Examiner* — Dawayne A Pinkney

(57) ABSTRACT

An apparatus is provided for finding and defining a prescription for reading glasses for an AMD patient whose Macula and Fovea are damaged enough that the patient has double vision, i.e. the patient sees two images of every object within the field of view of the Macula and Fovea. The apparatus positions reading lenses in various locations in front of the patient's eyes until the patient indicates that he/she now sees one image for each object in the field of view of the Macula and Fovea. The X-Y coordinates of the location of each lens axis in relation to the patient's visual axis are offset dimensions indicated for each eye by the apparatus and is thus the prescription for reading lenses.

4 Claims, 7 Drawing Sheets

(ENLARGED 2X)

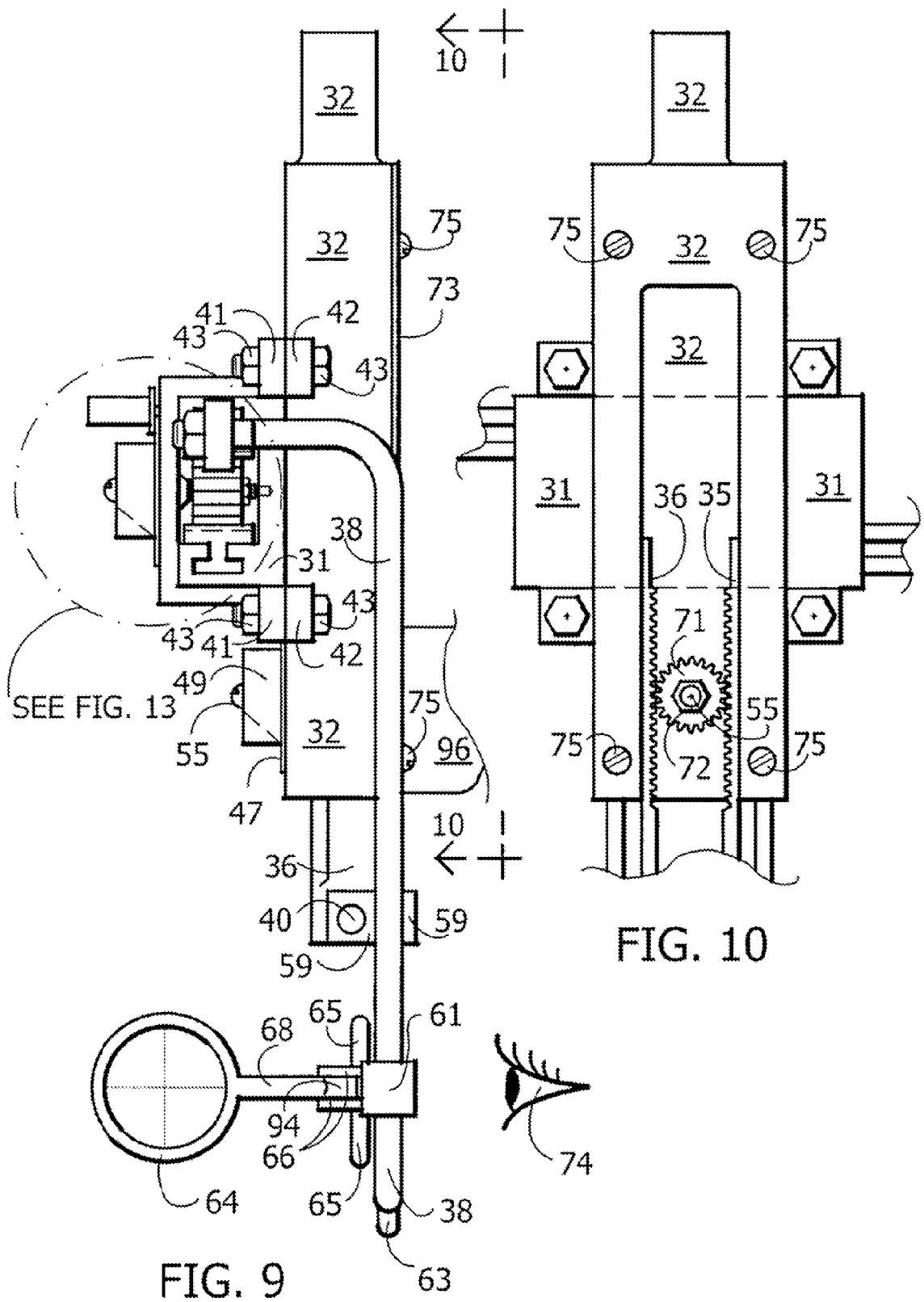

(ENLARGED 2X)

(ENLARGED 2X)

APPARATUS FOR DETERMINING PRESCRIPTION FOR READING LENSES FOR EYES WITH MILD AMD

CROSS REFERENCE TO RELATED PROVISIONAL APPLICATION

This non-provisional application claims the benefit of the filing date of U.S. Provisional Patent Application No. 61/319559 filed on 31 Mar. 2010 and titled "Calibration device for producing reading glasses lens for eyes with mild AMD", which is hereby incorporated by reference in its entirety.

LEXICON

X-Y Coordinates is an Engineering expression used throughout these Specifications, however, Opticians are more familiar with H&V (Horizontal and Vertical). Other expressions familiar to Opticians may be used at points in the Specifications as well as the Drawings.

Lens-blank means a round, polished lens that is edged to fit the lens-holders of the preferred embodiment.

Lens-set means two (OD and OS) lenses of each diopter power specified and plus and/or minus diopter specified.

Integral applied to components of the preferred embodiment, means that a component, that is said to be integral to a larger component, already named and defined, is cast with the said named component as a single homogeneous piece that can not be separated into individual parts.

BACKGROUND

Many people suffering from Adult-onset Macular Degeneration (AMD) have damage to the Macula that has repositioned the Fovea (center of the Macula) causing a new visual-axis to be slightly offset from the original (normal) visual-axis. This is very common in older people. The result in many cases is double vision. Double vision occurs when the image that one eye sees does not coincide with the image that the other eye sees when looking with both eyes at the same time at the same physical object, making it appear that there are two of everything in the field of view of the Macula and Fovea. The brain can accommodate for slight differences, but, when the offset becomes too great for the brain to accommodate—double vision results. Peripheral vision is not affected by AMD.

Many AMD patients still have relatively good acuity in the AMD eye but the offset of the visual-axis still results in double vision. For patients with AMD in both eyes, the result most likely will be double vision. AMD sufferers have to find their own method of coping with the problem of reading. One way to cope is to close one eye while reading with the eye having the best acuity. This quickly becomes tiring. Another method is to wear an eye-patch instead of closing the eye. The eye-patch interferes with reading glasses making that option also unsatisfactory. A problem with both methods is that the person looses the peripheral vision in that eye. Loosing peripheral vision can actually be dangerous if the person is reading in a dangerous industrial setting where it is important to see danger approaching with the periphery of ones vision. There has always been a need for a more satisfactory way of improving the reading ability of such individuals.

SUMMARY

I have had AMD for a number of years and relied on the methods mentioned in the Background above for reading and found them to be very unsatisfactory. I was constantly on the lookout for a way that was better. I noticed one day, while using a magnifying glass, that as the magnifying glass is moved across the page in one direction that the words on the printed page appeared to move in the opposite direction. Well, that was not news to me. What was new was me thinking that there may be a new use for the prism effect. So I theorized that if my reading glasses lens were relocated within their frames, let's say move one up and the other one down just the right distance, that an image of an object would focus on the center of each Fovea of my two eyes. In other words, the images might be relocated just the right distance and direction to come together and appear to me as one image (single vision) instead of two images (double vision) for each object viewed. Through experimentation I found my theory to be correct. As a matter of fact, it worked even better than I had hoped. So, it became obvious to me that there was a need for an apparatus that could quickly and accurately determine what those distances and directions are for any AMD patient. Those distances and directions plus the diopter strengths would then be the prescription for reading lenses for an AMD patient. Hereinafter those distances and directions are referred to as "offset distances (X-Y coordinates)".

BRIEF DESCRIPTION OF THE DRAWINGS

FIG. 9 is an orthographic side view of the preferred embodiment employing the principles of the present invention.

FIG. 10 is a partial orthographic back view of the preferred embodiment employing the principles of the present invention.

DETAILED DESCRIPTION

Figure 7:
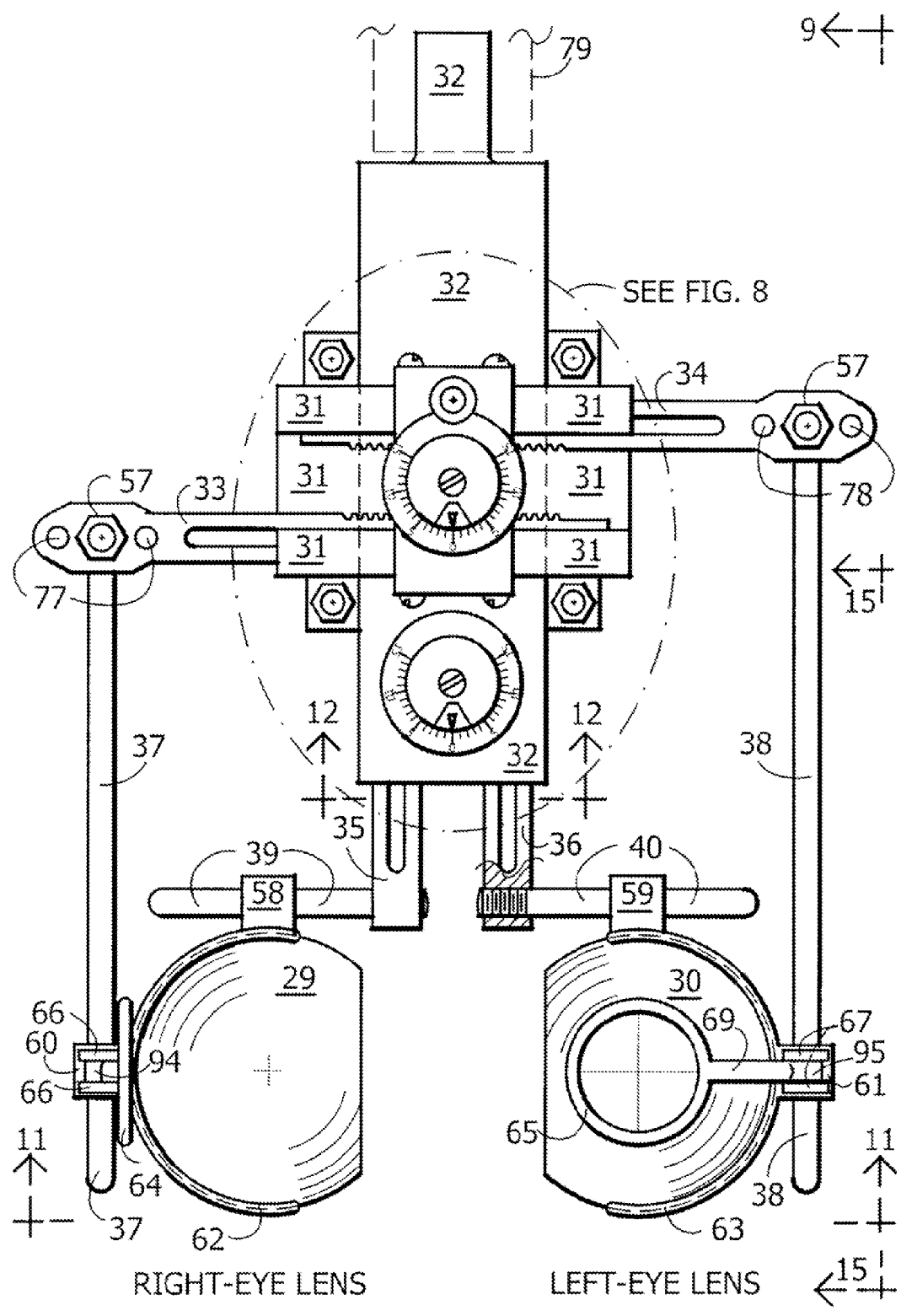
FIG. 7 is an orthographic front view of the preferred embodiment employing the principles of the present invention.

All references to "right" and "left" in these Specifications and Claims are relative to the AMD patient's perspective while viewing through a right lens 29 and a left lens 30 shown in FIG. 7, the front view of the preferred embodiment, also further clarified by the graphic of a patient's-eye 74 shown in FIG. 9, a side view.

Like referenced elements are represented by like reference numbers throughout the drawings. Referenced components shown in a particular Figure but not described herein under that Figure's heading is because the referenced component has already been described in detail in a discussion of a previous Figure.

Figure 1:
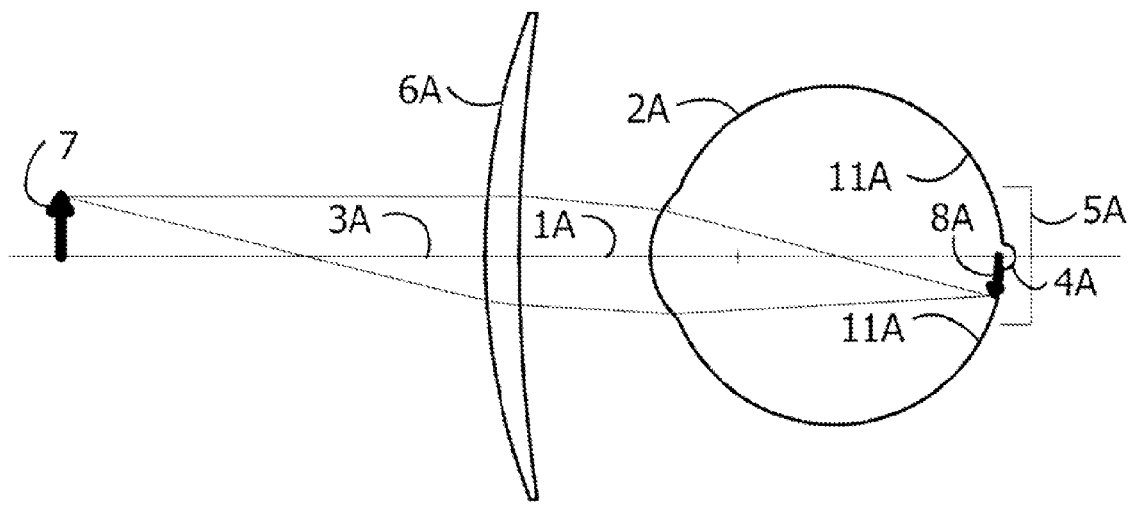
FIG. 1 is a side orthographic view of a normal eye (Emsley Standard Reduced 60-diopter eye), except for farsightedness, viewing an object through a magnifying lens.
Figure 2:
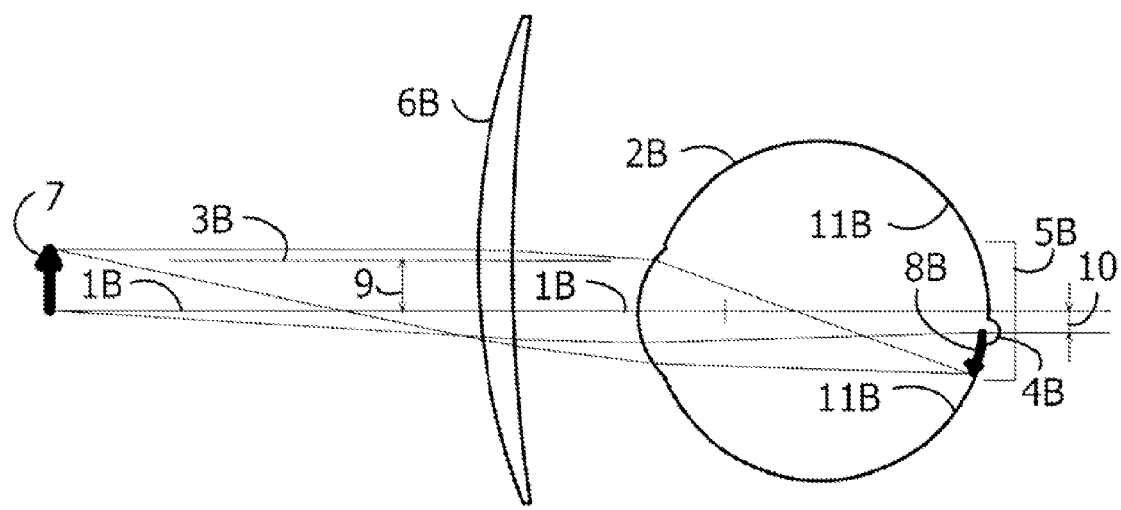
FIG. 2 is a side orthographic view of an eye (Emsley Standard Reduced 60-diopter eye) with farsightedness and AMD, viewing an object through a magnifying lens.

FIG. 1 is a side orthographic view of a normal eye (Emsley Standard Reduced 60-diopter eye) hereinafter referred to as ESR60-DE 2A, and it is assumed that it is normal except for farsightedness. Here it is shown viewing an object 7 through a first-magnifying-lens 6A the diopter strength of which has been determined by a conventional eye exam. A first-image 8A of the object 7 is formed upside down on a first-Fovea 4A and surrounding first-Macula 5A (size exaggerated for clarity). Surrounding the first-Macula 5A is a first-Retina 11A. For the purpose of illustrating how the first-image 8A is formed, light rays emanating from the object 7, and a first-magnifying-lens-axis 3A, and a first-visual-axis 1A are also shown. FIG. 2 is an orthographic side view of an eye (Emsley Standard Reduced 60-diopter eye) hereinafter referred to as AMD-ESR60-DE 2B, and it is assumed that in addition to farsightedness it is affected by AMD. Here it is shown viewing the object 7 through a second-magnifying-lens 6B. In this view the effects of AMD has shifted a second-Fovea 4B downward a small second-distance 10. A second-magnifying-lens-axis 3B of the second-magnifying-lens 6B is shifted upward an exact first-distance 9 required to cause a second-image 8B to form on the center of the second-Fovea 4B and (if large enough), on a second-Macula 5B which will make the object 7 appear to be in the same location in space as the normal eye (without AMD) sees it. Surrounding the second-Macula 5B is a second-Retina 11B. Thus with both eyes focusing on the object 7 it appears as one object.

If the second-magnifying-lens-axis 3B were to be aligned with a second-visual-axis 1B, that existed prior to the onset of AMD, then with both eyes open, the patient would see two separate objects 7 (one above the other). This is the case because the image formed in AMD-ESR60-DE 2B would not be centered on the second-Fovea 4B as it is in ESR60-DE 2A, thus the patient would see two objects 7 that do not coincide.

Figure 3:
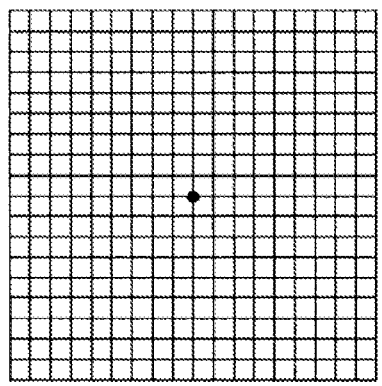
FIG. 3 is a graphic representation of how a standard Amsler Grid looks to a pair of normal eyes. It also represents how a standard Amsler Grid looks to a pair of eyes, one or both of which have mild AMD, but are viewing through corrective lenses embodying the principles of the present invention.

FIG. 3 is a graphic representation of how a standard Amsler Grid looks to a pair of normal eyes. It also represents how a standard Amsler Grid looks to a pair of eyes in which one or both of them has mild AMD but are viewing through corrective lenses embodying the principles of the present invention. The Amsler Grid may appear slightly blurry due to mild loss of acuity caused by AMD, but the lines will appear straight.

Figure 4:
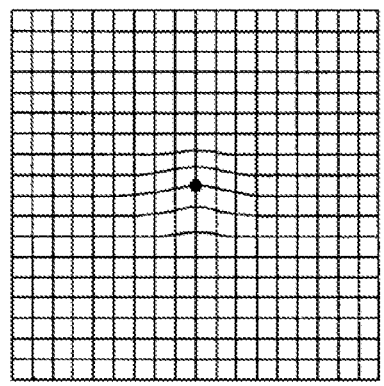
FIG. 4 is a graphic representation of how a standard Amsler Grid might look to an eye with mild AMD where the Fovea (center of the Macula) has shifted slightly downward creating a new visual-axis slightly offset from the original normal visual-axis.

FIG. 4 is a graphic representation of how the standard Amsler Grid might look to an eye with mild AMD, such as AMD-ESR60-DE 2B, viewing through an ordinary magnifying lens, where the Fovea 4B (center of the Macula) has shifted downward the small second-distance 10 away from the normal second-visual-axis 1B.

Figures 5, 6:
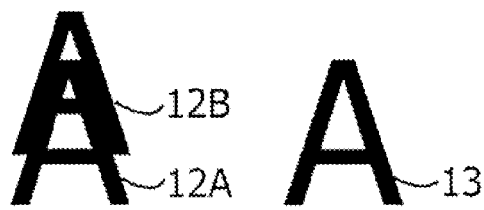
FIG. 5 is a graphic representation of how the alphabetical character "A" might look to a person with mild AMD in one or both eyes viewing with both eyes through ordinary reading lenses.
FIG. 6 is a graphic representation of how the alphabetical character "A" will look to a person with normal vision viewing with both eyes. It also represents how the alphabetical character "A" might look to a pair of eyes in which one or both of them has mild AMD but are viewing through corrective lenses embodying the principles of the present invention.

FIG. 5 is a graphic representation of how the alphabetical character "A" might look to a person viewing it with both eyes where one eye has a mild case of AMD such as AMD-ESR60-DE 2B, in which the Fovea 4B has shifted slightly downward away from the normal visual-axis 1B. The other eye could be normal such as ESR60-DE 2A or it could have mild AMD like AMD-ESR60-DE 2B but with the offset in a different direction and/or a different distance. A tiny shift is accommodated for by the brain which makes the viewer see only one "A", but eventually as the distortion becomes greater and greater, the brain can no longer accommodate so that the viewer then sees double. In this case, one "A" above another.

FIG. 6 is a graphic representation of how the alphabetical character "A" will look to a person with normal vision in both eyes. The images formed on the first-Fovea 4A and the first-Macula 5A of the two eyes coincide and appears to the viewer as one object. It also represents how the alphabetical character "A" might look to a pair of eyes in which one or both of them has mild AMD but are viewing through corrective lenses made using the principles of the present invention. The image may appear slightly blurry due to mild loss of acuity due to AMD.

Although the present inventor was able to make a pair of reading glasses by trial and error by using the principles of the present invention and the scientific principles described in FIG. 1 and FIG. 2, there needed to be an apparatus employing the principles of the present invention that would provide a quicker and more accurate way to find and define a prescription for lenses. The present inventor did conceive such an apparatus and it is the "preferred embodiment" shown in the Drawings, FIG. 7 through FIG. 13 and FIG. 15. Plain magnifying lenses with a diopter strength appropriate for a selected patient could be positioned in front of the patient by some mechanical means that could move the lenses slowly horizontally gradually closer together or gradually farther apart until the patient sees some sign of improved vision. And, there needed to be a similar provision for vertical movement of the two lenses whereby they would move slowly in opposite directions until the patient sees some sign of further improved vision. The preferred embodiment satisfies both of those criteria.

Figure 8:
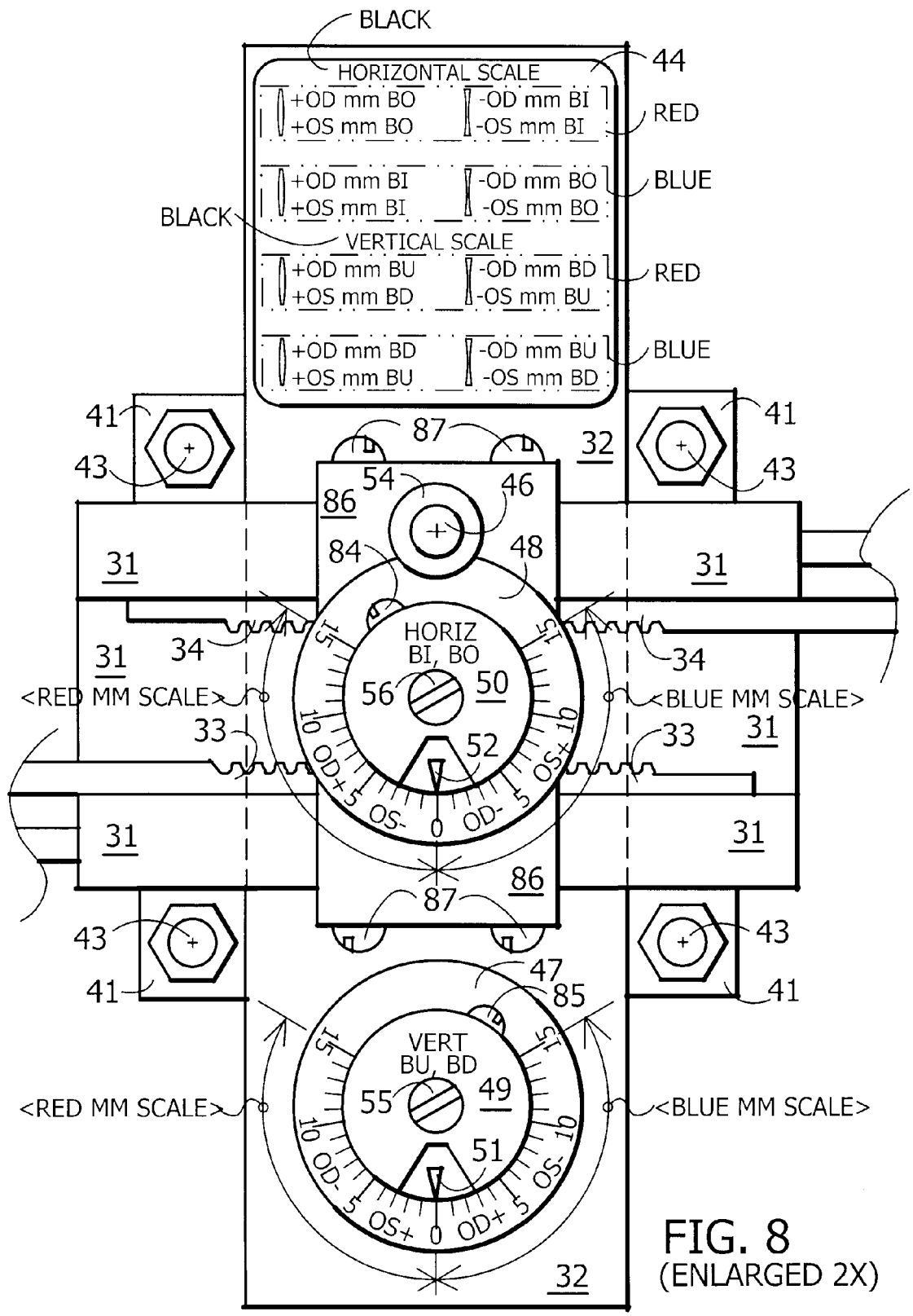
FIG. 8 is an enlarged partial front view of the preferred embodiment employing the principles of the present invention.

FIG. 7 and FIG. 8 illustrate the front view and a partial enlarged front view respectively of the preferred embodiment, employing the principles of the present invention. Components pertinent to the discussion of FIG. 7 and FIG. 8 but that are more clearly shown in other Figures are so noted. The front view clearly shows linkages between a horizontal-adjustment-knob 50 (a first human interface) and a right-lens-blank 29. Likewise linkages between the horizontal-adjustment-knob 50 and a left-lens-blank 30 are shown. A vertical-adjustment-knob 49 (a second human interface) is shown linked to the right-lens-blank 29. Likewise linkages between the vertical-adjustment-knob 49 and the left-lens-blank 30 are shown. These linkages provide the basic motions necessary for the lenses, but, more detail is provided below for greater clarity.

Figure 13:
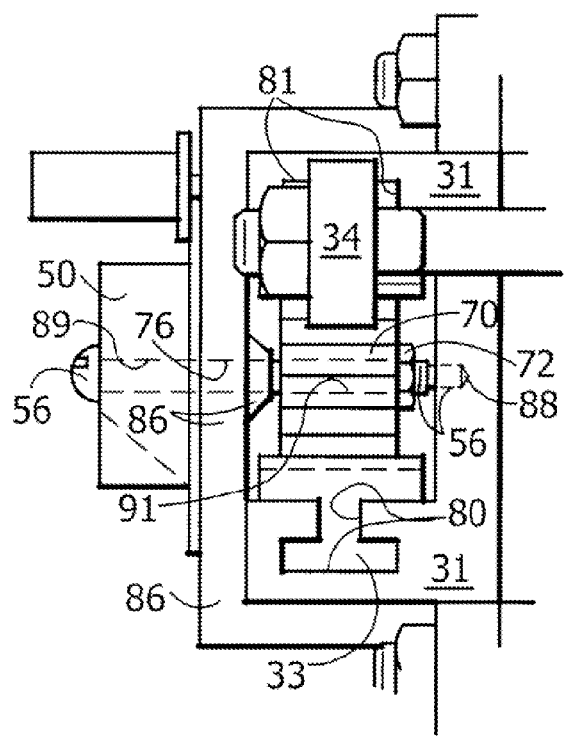
FIG. 13 is a partial side view taken from FIG. 9.

Horizontal Control: Horizontal movement of the right-lens-blank 29 begins with the horizontal-adjustment-knob 50 that has a first-central-hole 89 (FIG. 13) along its axis sized to accept a horizontal-pinion-axle 56 that passes through the first-central-hole 89 (FIG. 13) and is prevented from rotating within the horizontal-adjustment-knob 50 by a first-setscrew 84. Further, the horizontal-pinion-axle 56 passes through a slip-fit-hole 76 (FIG. 13) in a bearing-plate 86 and through a horizontal-pinion 70 (FIG. 13) and finally terminates in a bearing-hole 88 (FIG. 13) in a horizontal-guide 31. The bearing-plate 86 is held in place with four bearing-plate-fasteners 87. A locknut 72 (FIG. 13) on the horizontal-pinion-axle 56 confines the horizontal-pinion 70 (FIG. 13) to it's required position on the horizontal-pinion-axle 56. The portion of the horizontal-pinion-axle 56 that fits within the horizontal-pinion 70 (FIG. 13) is non-round in cross section matching a non-round-hole 91 (FIG. 13) in the center of the horizontal-pinion 70 (FIG. 13) whereby any rotation of the horizontal-adjustment-knob 50 results in an equal rotation of the horizontal-pinion 70 (FIG. 13).

The horizontal-guide 31 has a bottom-horizontal-T-shaped groove 80 (FIG. 13) and a top-horizontal-T-shaped-groove 81 (FIG. 13) running parallel to each other and spaced apart far enough to accommodate a bottom-horizontal-rack 33 and a top-horizontal-rack 34, each respective rack has a T-shaped cross section that matches and engages the T-shaped grooves in the horizontal-guide 31 wherein the horizontal-pinion 70 (FIG. 13) is juxtaposed between and engages both the bottom-horizontal-rack 33 and the top-horizontal-rack 34 causing them to slide equal distances but in opposite directions when the horizontal-adjustment-knob 50 is rotated.

A right-vertical-rod 37 is fixedly attached to a right end of the bottom-horizontal-rack 33 through the use of a vertical-rod-fastener 57 and two right-lateral-stability-pins 77 integral to the right-vertical-rod 37 and the right-vertical-rod 37 is vertically slidably connected to a right-vertical-rod-bushing 60 which is integral to a right-lens holder 62 so that the right-lens-holder 62 is free to slide vertically along the length of the right-vertical-rod 37 when it is propelled to do so by a right-horizontal-rod 39, but its horizontal movement is restrained by the right-vertical-rod 37. The end result of the foregoing detailed linkages is that horizontal motion of the bottom-horizontal-rack 33 imparts an equal motion to the right-lens-holder 62.

A left-vertical-rod 38 is fixedly attached to a left end of the top-horizontal-rack 34 through the use of the vertical-rod-fastener 57 and two left-lateral-stability-pins 78 integral to the left-vertical-rod 38 and the left-vertical-rod 38 is vertically slidably connected to a left-vertical-rod-bushing 61 which is integral to a left-lens holder 63 so that the left-lens-holder 63 is free to slide vertically along the length of the left-vertical-rod 38 when it is propelled to do so by a left-horizontal rod 40, but its horizontal movement is restrained by the left-vertical-rod 38. The end result of the foregoing detailed linkages is that horizontal motion of the top-horizontal-rack 34 imparts an equal motion to the left-lens-holder 63.

Figure 12:
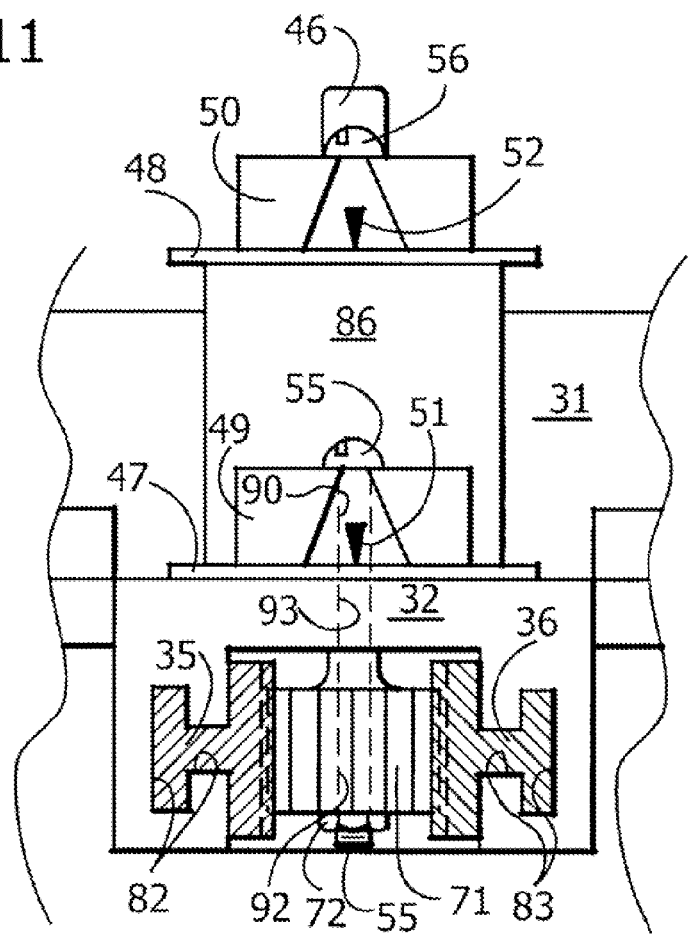
FIG. 12 is a section taken horizontally through FIG. 7, looking up.

Vertical Control: Vertical movement of the right-lens-blank 29 begins with the vertical-adjustment-knob 49 that has a second-central-hole 90 (FIG. 12) along its axis sized to accept a vertical-pinion-axle 55 that passes through the second-central-hole 90 and is prevented from rotating within the vertical-adjustment-knob 49 by a second-setscrew 85. Further, the vertical-pinion-axle 55 passes through a second-slip-fit-hole 93 (FIG. 12) in a vertical guide 32 and through a vertical-pinion 71 (FIG. 12). The locknut 72 (FIG. 12) on the vertical-pinion-axle 55 confines the vertical-pinion 71 (FIG. 12) to its required position on the vertical-pinion-axle 55. The portion of the vertical-pinion-axle 55 that fits within the vertical-pinion 71 (FIG. 12) is non-round in cross section matching a non-round-hole 92 (FIG. 12) in the center of the vertical-pinion 71 (FIG. 12) whereby any rotation of the vertical-adjustment-knob 49 results in an equal rotation of the vertical-pinion 71 (FIG. 12).

The vertical-guide 32 has a right-vertical-T-shaped-groove 82 (FIG. 12) and a left-vertical-T-shaped-groove 83 (FIG. 12) running parallel to each other and spaced apart far enough to accommodate a right-vertical-rack 35 and a left-vertical-rack 36, each respective rack has a T-shaped cross section that matches and engages the T-shaped grooves in the vertical-guide 32 wherein the vertical-pinion 71 (FIG. 12) is juxtaposed between and engages both the right-vertical-rack 35 and the left-vertical-rack 36 causing them to slide equal distances but in opposite directions when the vertical-adjustment-knob 49 is rotated.

The right-horizontal-rod 39 is tightly threaded into a bottom end of the right-vertical-rack 35 and the right-horizontal-rod 39 is horizontally slidably connected to a right-horizontal-rod-bushing 58 which is integral to the right-lens-holder 62 so that the right-lens-holder 62 is free to slide horizontally along the length of the right-horizontal-rod 39 when it is propelled to do so by the right-vertical-rod 37, but its vertical movement is restrained by the right-horizontal-rod 39. The end result of the foregoing detailed linkages is that vertical motion of the right-vertical-rack 35 imparts an equal motion to the right-lens-holder 62.

The left-horizontal-rod 40 is tightly threaded into a bottom end of the left-vertical-rack 36 and the left-horizontal-rod 40 is horizontally slidably connected to a left-horizontal-rod-bushing 59 which is integral to the left-lens-holder 63 so that the left-lens-holder 63 is free to slide horizontally along the length of the left-horizontal-rod 40 when it is propelled to do so by the left-vertical-rod 38, but its vertical movement is restrained by the left-horizontal-rod 40. The end result of the foregoing detailed linkages is that vertical motion of the left-vertical-rack 36 imparts an equal motion to the left-lens-holder 63.

Crosshairs and Lens-holders: The right-lens-blank 29 is forced into a groove in the right-lens-holder 62 and is held in place by tension due to the right-lens-holder 62 having a slightly smaller diameter than the right-lens-blank 29 by an amount sufficient to prevent the right-lens-blank 29 from falling out; likewise for the left-lens-blank 30 and the left-lens-holder 63. It is important to provide a crosshairs attachment for each eye so that the right-lens-blank 29 and the left-lens-blank 30 can be accurately centered on the patient's eyes by swinging a right-crosshairs 64 and a left-crosshairs 65 in front of the patients eyes and adjusting a spacing of the pair of crosshairs 64 and 65 by rotating the horizontal-adjustment-knob 50 until the spacing of the pair of crosshairs 64 and 65 matches a spacing of the patient's eyes. The right-crosshairs 64 (shown in idle position, but is more clearly shown in FIG. 9) has an integral right-extension-arm 68 (FIG. 9) terminating in a single integral right-arm-hinge-knuckle 94 that is rotatably pinned to a pair of right-hinge-knuckles 66 both of which are integral to the right-vertical-rod-bushing 60. The left-crosshairs 65 has an integral left-extension-arm 69 terminating in a single integral left-arm-hinge-knuckle 95 that is rotatably pinned to a pair of left-hinge-knuckles 67 both of which are integral to the left-vertical-rod-bushing 61.

Figure 14:
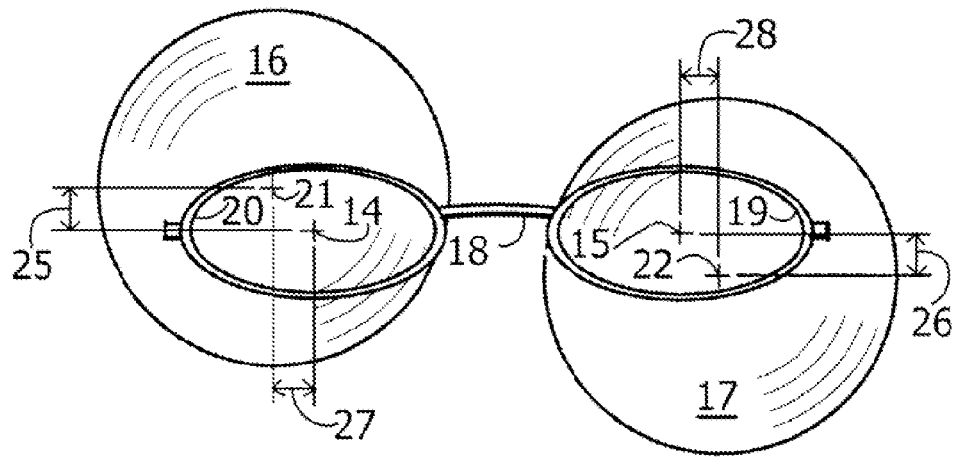
FIG. 14 illustrates how the offset distances (X-Y coordinates) obtained from an examination of an AMD patient's eyes, using an apparatus employing the principles of the present invention, become the prescription and then are translated into the actual orientation of each respective lens-axis in relation to the location of each respective frame's visual-axis.

Zeroing: At this point (after aligning crosshairs with eyes) a circular horizontal-scale 48 is rotated until zero on the scale aligns with a single horizontal-index 52 printed on the horizontal-adjustment-knob 50 and a zeroing-thumbscrew 46 is tightened thereby clamping the rotatable horizontal-scale 48 between a zeroing-thumbscrew-washer 54 and the bearing-plate 86. This is called "zeroing" the scale and equally divides the horizontal "offset" distance (determined during an examination of a patient) between the right and left lenses that are selected by a technician to fit eyeglass frames that are selected by the patient. FIG. 14 provides more detail regarding offset.

User Instructions: The horizontal-scale 48 and the vertical-scale 47 are both circular scales with millimeter indications ranging from zero to fifteen on each side of a zero. On both scales the right side numerals and indexes are red and on the left side are blue. This is a color code for use with a user-instructions 44 that clearly indicates whether a number on the horizontal-scale 48 aligned with the horizontal-index 52 is indicating a distance that is BI or BO for the patient's OD and BI or BO for the patient's OS. Likewise for a number aligned with the vertical-index 51, the color code in the instructions 44 indicates whether the distance is BU or BD for the patient's OD and BU or BD for the patient's OS.

Interfacing with an articulated arm: A top extension of the vertical-guide 32 is formed to accept a fitting on a commercially available articulated-arm 79 that can be used for positioning the preferred embodiment in front of the patient's eyes. See FIG. 9 for a description of four front-lugs 41 and four lug-fasteners 43.

Figure 15:
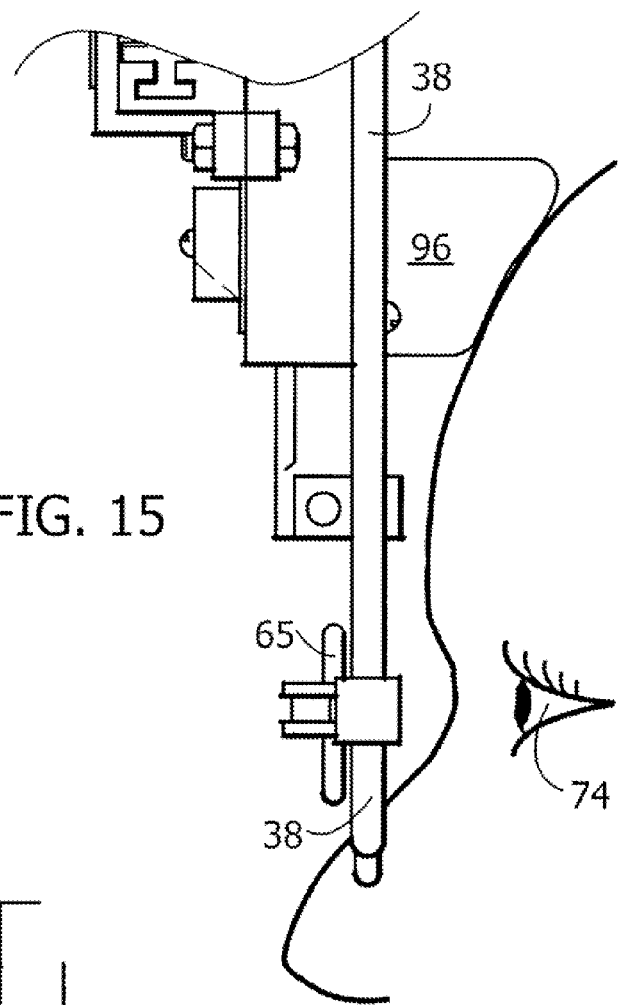
FIG. 15 illustrates a forehead-rest that steadies the embodiment in relation to the patient's eyes. It is attached to the patient's side of the embodiment with adhesive to a transparent gear-cover.

FIG. 9 illustrates the side view of the preferred embodiment, employing the principles of the present invention. A transparent-gear-cover 73, and transparent-gear-cover-fasteners 75 are described under FIG. 10. A human eye 74 is self explanatory. This is the best view in which to discuss the means for securely fastening the horizontal-guide 31 to the vertical-guide 32. Four front-lugs 41 are provided integral to the horizontal-guide 31 flush with the back side of the horizontal-guide 31. These lugs align with four back-lugs 42 provided integral to the vertical-guide 32 which are flush with the front side of the vertical-guide 32. All four pairs of lugs are fastened together with sufficient structural integrity with four sets of bolt and nut lug-fasteners 43. A forehead-rest 96 is shown broken away. A full view of it is shown in FIG. 15. Refer to FIG. 7 and FIG. 8 for a description of other referenced components.

FIG. 10 is an orthographic back view of the preferred embodiment. This shows the gear teeth of the vertical-pinion 71 engaging both the right-vertical-rack 35 and the left-vertical-rack 36 gear teeth. It is so open and accessible that a transparent-gear-cover 73 (invisible in this view) is provided to prevent a patient's hair from getting tangled in the gears. The transparent-gear-cover 73 has a height and width matching the vertical-guide 32 and is secured in place with fasteners 75. The forehead-rest 96 is not shown so the relationship between the pinion 71 and the two racks 35 and 36 can be clearly shown. The horizontal-guide 31 is shown behind the vertical-guide 32. The vertical-pinion 71 is shown held in place on the vertical pinion-axle 55 by the locknut 72.

Figure 11:
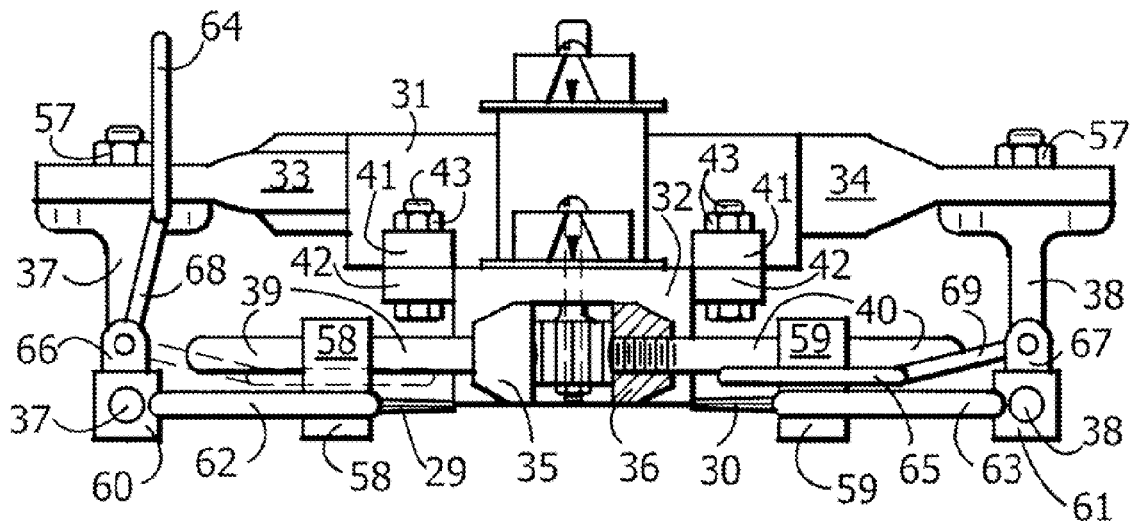
FIG. 11 is an orthographic bottom view of the preferred embodiment employing the principles of the present invention.

FIG. 11 illustrates the bottom view of the preferred embodiment, employing the principles of the present invention. Refer to FIG. 7 and FIG. 8 for a complete description of the components referenced, except the forehead-rest 96 is not referenced in FIG. 7 and FIG. 8. See FIG. 15 for a complete description of the forehead-rest 96.

FIG. 12 Illustrates a partial section view taken through FIG. 7. Components of particular interest in this view are the right-vertical-T-shaped-groove 82 and the left-vertical-T-shaped-groove 83 in which the right-vertical-rack 35 and the left-vertical-rack 36 respectively slide up and down in the vertical-guide 32 in opposite directions as the vertical-adjustment-knob 49 is rotated clockwise and counterclockwise. Due to the connection of the vertical-adjustment-knob 49 to the vertical-pinion 71 through the vertical-pinion-axle 55, the rotational movement of the vertical-pinion 71 mimics the rotation of the vertical-adjustment-knob 49. The vertical-pinion-axle 55 passes through the second-central-hole 90, the second-slip-fit-hole 93 and the second-non-round-hole 92 in the vertical-pinion 71. The vertical-pinion 71 is held in its proper place by the locknut 72.

FIG. 13 illustrates a partial side view taken from FIG. 9. Components of particular interest in this partial view are the ones interconnecting the horizontal-adjustment-knob 50 with the sliding movement of the bottom-horizontal-rack 33 and the top-horizontal-rack 34 within the bottom-horizontal-T-shaped-groove 80 and the top-horizontal-T-shaped groove 81, both within the horizontal-guide 31. The horizontal-pinion-axle 56 passes through the first-central-hole 89 in the center of the horizontal-adjustment-knob 50 and is prevented from rotating within the first-central-hole 89 by the first-set-screw 84 (hidden in this view). The horizontal-pinion-axle 56 continues on through the first-slip-fit-hole 76 in the bearing-plate 86 and on through the first-non-round-hole 91 in the horizontal-pinion 70 and terminating in the bearing-hole 88. The locknut 72 holds the horizontal-pinion 70 in its proper place. Refer to FIG. 7 and FIG. 8 for a complete description of other components referenced.

FIG. 14 illustrates how a right-lens-blank-axis 21 of a right-lens-blank 16 is above a right-frame-visual-axis 14 by a right-vertical-distance 25 as determined by an eye exam employing the principles of the present invention; the right-lens-blank-axis 21 is to the right of the right-frame-visual-axis 14 by a right-horizontal-distance 27 as determined by the same eye exam.

Likewise FIG. 14 illustrates how a left-lens-blank-axis 22 of a left-lens-blank 17 is below a left-frame-visual-axis 15 by a left-vertical-distance 26 and the left-lens-blank-axis 22 is to the left of the left-frame-visual-axis 15 by a left-horizontal-distance 28 as determined by the same eye exam.

It can now be seen that with this prescription, a commercially available edging machine can be used to grind the right-lens-blank 16 to fit a right-lens-cut-line 20 and the left-lens-blank 17 to fit a left-lens-cut-line 19 so both lenses can be mounted in eyeglass-frames 18 for use by an AMD patient for improved reading ability.

FIG. 15 illustrates the forehead-rest 96 that steadies the embodiment in relation to the patient's eyes 74. It is attached with adhesive to the transparent gear-cover 73 (hidden by the left-vertical-rod 38). The forehead-rest 96 is positioned and fixedly attached to the patient side of the apparatus to press against the patient's forehead when the eyes align with the centers of a pair of crosshairs 64 and 65 (crosshairs 64 is hidden by crosshairs 65) wherein the forehead-rest 96 is constructed of a soft spongy material similar to a plastic covered foam armrest of a luxury automobile.

The foregoing merely illustrates the principles of the invention. For example, although the means for positioning the lens in front of the patient's eyes in the illustrated embodiment are rack and pinion gears, other means are possible such as threaded screws. The millimeter scales could be a different unit. The circular scales and the indexes on round knobs could be changed to linear scales affixed to the racks with single indexes affixed to the vertical guide and the horizontal guide. The lens used for positioning in front of the patient's eyes could accommodate astigmatism as well as farsightedness. The sliding fit of the four rod bushings could be replaced with linear-ball bearings. Instead of dividing the correction (X-Y coordinates) equally between two lenses, the whole correction could be incorporated into one lens in cases where the offset distances are relatively small (for example less than 8 mm total).

It will thus be appreciated that those skilled in the art will be able to devise numerous alternative arrangements that, while not shown or described herein, employ the principles of the invention and thus are within its spirit and scope.

What is claimed is:

1. An apparatus having a pair of lens holders, containing spherical lens blanks, oriented such that the lenses' axes are parallel to, but not centered on, a patient's visual axis (line-of-sight) and moves the lenses in infinitely variable increments, in response to user operated controls, in any direction in a plane which is perpendicular to the patient's line-of-sight; the controls move the OD lens in a direction which is always opposite the direction of the OS lens, but equal in distance, thus automatically splitting the prism diopters thereby induced; means for an Ophthalmologist to read a prism diopter Rx in Prescriber's Notation directly from the apparatus without the need for computer calculations, the means comprising:

a means for moving the pair of lens blanks in a plane that is perpendicular to the patient's line-of-light;

a means for indicating in millimeters, without the need for computer calculations, the amount of horizontal and vertical decentration present, at any location in the plane, in each respective lens-holder;

a means for preventing the two lenses from interfering with each other even when a space between centers is less than the Patient's PD;

a means for zeroing the apparatus at a point of horizontal movement of the lens-holders whereat the spacing of the centers of the lens-holders matches the patient's PD;

means for moving the pair of lens-blanks, in the plane that is perpendicular to the patient's line-of-sight, by a horizontal and a vertical decentration (H-V coordinates) that induces the necessary prism that in turn causes the double images that the patient sees to fuse, the means comprising:

a horizontal-guide that has a bottom-horizontal-T-shaped-groove and a top-horizontal-T-shaped-groove facing each other and running parallel to each other and spaced apart far enough from each other to accommodate a bottom-horizontal-rack and a top-horizontal-rack;

two racks each having a T-shaped cross section that engages each respective T-shaped-groove in the horizontal-guide in which the gear teeth face each other and a horizontal-pinion is juxtaposed between the bottom-horizontal-rack and the top- horizontal-rack so that rotating a horizontal-pinion-axle rotates the horizontal-pinion that engages the bottom-horizontal-rack and the top-horizontal-rack and causes them to slide equal distances but in opposite directions within the bottom-T-shaped-groove and the top-T-shaped-groove in the horizontal-guide;

a right-vertical-rod fixedly attached to a right end of the bottom-horizontal-rack and vertically slidably connected to a right-lens-holder whereby horizontal motion of the bottom-horizontal-rack imparts an equal motion to the right-lens-holder;

a left-vertical-rod fixedly attached to a left end of the top-horizontal-rack and vertically slidably connected to a left-lens-holder whereby horizontal motion of the top-horizontal-rack imparts an equal motion to the left-lens-holder;

a vertical-guide fixedly attached to and at right angles to the horizontal-guide, in which the vertical-guide has a right-vertical-T-shaped-groove and a left-vertical-T-shaped-groove facing each other and running parallel to each other and spaced apart far enough to accommodate a right-vertical-rack and a left-vertical-rack; two racks, each having a T-shaped cross section that engages the right-vertical-T-shaped-groove and the left-vertical-T-shaped-groove in the vertical-guide in which the gear teeth face each other and a vertical-pinion is juxtaposed between the right-vertical-rack and the left-vertical-rack so that rotating a vertical-pinion-axle rotates the vertical-pinion that engages the right-vertical-rack and the left-vertical-rack and causes them to slide equal distances but in opposite directions within the right-vertical-T-shaped-groove and the left-vertical-T-shaped-groove in the vertical-guide;

a right-horizontal-rod fixedly attached to a bottom end of the right-vertical-rack and horizontally slidably connected to the right-lens-holder whereby vertical motion of the right-vertical-rack imparts an equal motion to the right-lens-holder; and a left-horizontal-rod fixedly attached to a bottom end of the left-vertical-rack and horizontally slidably connected to the left-lens-holder whereby vertical motion of the left-vertical-rack imparts an equal motion to the left-lens-holder.

2. The invention of claim 1 in which the means for indicating in millimeters the H-V coordinates of the center of each respective lens-holder in relation to the patient's line-of-sight and the means for reading directly from the apparatus the prism diopter Rx in Prescriber's Notation, the means comprising:

a horizontal-adjustment-knob, for the H coordinate, fixedly attached to the horizontal-pinion-axle so that rotation of the horizontal-adjustment-knob causes equal rotation of the horizontal-pinion;

a circular color coded horizontal-scale centered on the horizontal-pinion-axle and restrained from rotating by a zeroing-thumbscrew and a washer thus clamping the horizontal-scale between the washer and a bearing-plate which is fixedly attached to the horizontal-guide whereby colored numbers on the horizontal-scale coordinate with colors in a user-instructions on the apparatus therein indicating, without the need for computer calculations, whether a decentration amount on the horizontal-scale which is aligned with a horizontal-index on the horizontal-adjustment-knob represents millimeters of induced prism Base-In (BI) or Base-out (BO) for each respective lens-holder;

a vertical-adjustment-knob for the V-coordinate fixedly attached to the vertical-pinion-axle so that rotation of the vertical-adjustment-knob causes equal rotation of the vertical-pinion; and a circular color coded vertical-scale centered on the vertical-pinion-axle and fixedly attached to the vertical-guide whereby colored numbers on the vertical-scale coordinate with colors in the user-instructions on the apparatus therein indicating, without the need for computer calculations, whether a decentration amount on the vertical-scale which is aligned with a vertical-index on the vertical-adjustment-knob represents millimeters of induced prism Base-Up (BU) or Base-Down (BD) for each respective lens-holder.

3. The invention of claim 2 in which:

the means for preventing interference between two installed lens-blanks is to cut a segment from all lens-blanks in the set so that when a pair of lens-blanks are installed in the apparatus and moved horizontally so that a center-to-center spacing of the two lens-blanks is less than the patient's PD, the lens-blanks are manually rotated within a right-lens-holder and a left-lens-holder so that the straight edges are facing each other; and conversely, the lens-blanks are manually rotated in the lens-holders so that the straight edges of the lens-blanks are facing away from each other when the apparatus is adjusted so that the center-to-center spacing of the lens-blanks are wider than the patient's PD.

4. The invention of claim 3 in which the means for zeroing the apparatus at a point of horizontal movement of the lens-holders whereat the spacing of the centers of the lens-holders matches the patient's PD, the means comprising:
  operating the horizontal-adjustment-knob until the spacing of a right-crosshairs and a left-crosshairs, hingedly connected to and centered on the corresponding movable-lens-holders, coincide with the patient's PD;
  rotating the circular color coded horizontal-scale until zero on the horizontal-scale is aligned with the horizontal-index printed on the horizontal-adjustment-knob which is fixedly attached to the horizontal-pinion-axle;
  tightening the zeroing-thumbscrew thus clamping the horizontal-scale between the washer and the bearing-plate thereby locking the crosshairs' spacing at the orientation where it matches the patient's PD.

* * * * *